United States Patent
Tanaka et al.

(10) Patent No.: US 6,824,760 B2
(45) Date of Patent: Nov. 30, 2004

(54) IMAGING AGENTS, PRECURSORS THEREOF AND METHODS OF MANUFACTURE

(75) Inventors: Akira Tanaka, Ehime (JP); Tomio Inoue, Gunma (JP); Katsumi Tomiyoshi, Tokyo (JP); David J. Yang, Sugar Land, TX (US); E. Edmund Kim, Houston, TX (US)

(73) Assignee: The University of Texas System, Austin, TX (US)

( * ) Notice: Subject to any disclaimer, the term of this patent is extended or adjusted under 35 U.S.C. 154(b) by 19 days.

(21) Appl. No.: 09/872,156

(22) Filed: Jun. 4, 2001

(65) Prior Publication Data

US 2003/0124059 A1 Jul. 3, 2003

(51) Int. Cl.$^7$ .............................................. A61K 51/00
(52) U.S. Cl. ..................................... 424/1.85; 424/1.89
(58) Field of Search .............................. 424/1.81, 1.85, 424/1.89; 548/469, 482, 484; 514/254.09; 562/433

(56) References Cited

U.S. PATENT DOCUMENTS 4,925,651 A * 5/1990 Coenen et al. ............. 424/1.85

OTHER PUBLICATIONS

Tomiyoshi et al, "Synthesis of isomers of $^{18}$F–labelled amino acid radiopharmaceutical: Position 2– and 3–$_L$–$^{18}$F–α–methyltyrosine using a separation and purification system", Nuclear Medicine Communications, 1997, 18, pp. 169–175.

Tomiyoshi et al, "Metabolic studies of [$^{18}$F–α–methyl] tyrosine in mice bearing colorectal carcinoma LS–180", Anti Cancer Drugs 1999, 10, pp. 329–336.

Wester, et al., "Synthesis and radiopharmacology of O–(2–[$^{18}$F]fluoroethyl)–L–Tyrosine for Tumor Imaging", The Journal of Nuclear Medicine, vol. 40, No. 1, Jan. 1999.

* cited by examiner

*Primary Examiner*—Michael G. Hartley
(74) *Attorney, Agent, or Firm*—Arent Fox, PLLC.

(57) ABSTRACT

Compounds of formula (I) and (II):

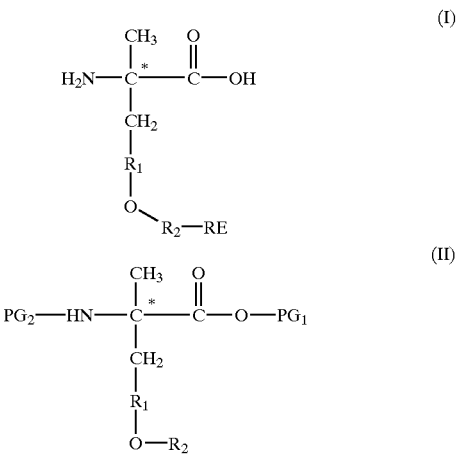

wherein groups $R_1$, $R_2$, RE, $PG_1$ and $PG_2$ have the definitions provided in the specification, methods of manufacture and methods of use.

14 Claims, No Drawings

IMAGING AGENTS, PRECURSORS THEREOF AND METHODS OF MANUFACTURE

BACKGROUND OF THE INVENTION

Short half-lived radioactive compounds are useful as imaging agents to diagnose cancers and abscesses. In the routine production of such imaging agents, safety and production considerations must be taken into account. It is advantageous to minimize contact time while ensuring quick and consistent production of the imaging agents.

There are generally two types of imaging procedures conducted. In positron emission tomography (PET), two beta rays emitted from the decaying radionuclide are detected. In single photon emission computed tomography (SPECT), one beta ray emitted from the decaying radionuclide is detected. PET provides a more exact location of tumors. However, SPECT is simpler and easier to use, and is therefore used more often.

Generally speaking, PET uses radio-compounds labeled with the positron-emitters such as $^{18}F$, $^{11}C$, $^{13}N$ and $^{15}O$, SPECT uses radio compounds labeled with the single-photon-emitters such as $^{18}F$, $^{11}C$, $^{13}N$ and $^{15}O$, although $^{75}Br$ and $^{124}I$ can also be used. SPECT, on the other hand, generally uses radionuclides that have more neutrons than protons, such as $^{67}Ga$, $^{77}Br$, $^{123}I$, $^{124}I$, $^{125}I$, $^{126}I$, $^{131}I$ and $^{201}Tl$.

In the art, glucose-based and amino acid-based compounds have been used as imaging agents. Amino acid-based compounds are more useful in analyzing tumor cells, due to their faster uptake and incorporation into protein synthesis. Of the amino acid-based compounds, $^{11}C$- and $^{18}F$-containing compounds have been used with success. $^{11}C$-containing radiolabeled amino acids suitable for imaging include, for example, L-[1-$^{11}C$]leucine (Keen et al. *J. Cereb. Blood Flow Metab.* 1989 (9):429–45), L-[1-$^{11}C$]tyrosine (Wiesel et al. *J. Nucl. Med.* 1991 (32):2041–49), L-[methyl-$^{11}C$]methionine (Comar et al. *Eur. J. Nucl. Med.* 1976 (1):11–14) and L-[1-$^{11}C$]methionine (Bolster et al. *Appl. Radiat. Isot.* 1986 (37):1069–70). However, $^{11}C$-containing radiolabeled amino acids have limited applicability, due to the short half-life of $^{11}C$ ($T_{1/2}$ =20 min.). Therefore, great effort was directed toward the synthesis and evaluation of other radionuclides, such as those listed above. Two $^{18}F$-containing radiolabeled amino acids, 4-[$^{18}F$]fluoro-L-phenylalanine and 2-[$^{18}F$]fluoro-L-tyrosine, exhibit protein incorporation, but can only be synthesized with uncorrected yields less than 5%. See Arnstein et al. *Biochem. J.* 1984 (1):340–46 and Coenen et al. *Radioisot. Klinik. Forschung* 1988 (18):402–40.

More recently, position 2- and 3-L-[$^{18}F$]fluoro-α-methyl tyrosine have been synthesized by electrophilic substitution (Tomiyoshi et al. *Nucl. Med. Commun.* 1997 (18):169–75). Unfortunately, the radiochemical yield from such a production is low. Another more recent compound to be synthesized is o-(2-[$^{18}F$]fluoroethyl)-L-tyrosine (Wester et al. *J. Nucl. Med.* 1999 (40):205–212). This paper describes the synthesis of the target compound, using a nucleophilic reaction, in a 40–60% yield. However, the reaction requires a two-step synthesis.

SUMMARY OF THE INVENTION

An object of the present invention is to develop new imaging agents suitable for use in PET and SPECT and which overcome the disadvantages of known compounds.

Another object of the present invention is to provide a method of manufacturing such compounds via the nucleophilic route using a one-step synthesis.

A further object of the invention is to provide precursors useful for manufacturing the new imaging agents of the invention.

These objects are achieved by the present invention.

The present invention includes compounds of formula (I), or pharmaceutically acceptable salts thereof:

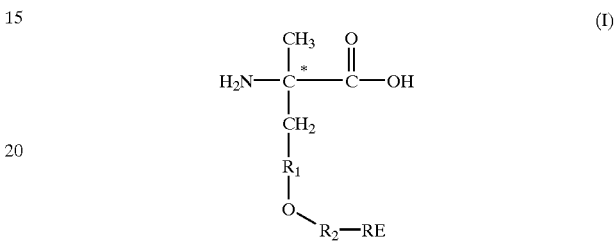

wherein the C marked with an asterisk represents a chiral center and the compound is present in the L-form, the D-form or as a racemic mixture;

$R_1$ is selected from the group consisting of a single bond, phenyl, and a group of formula (a), (b), (c) or (d)

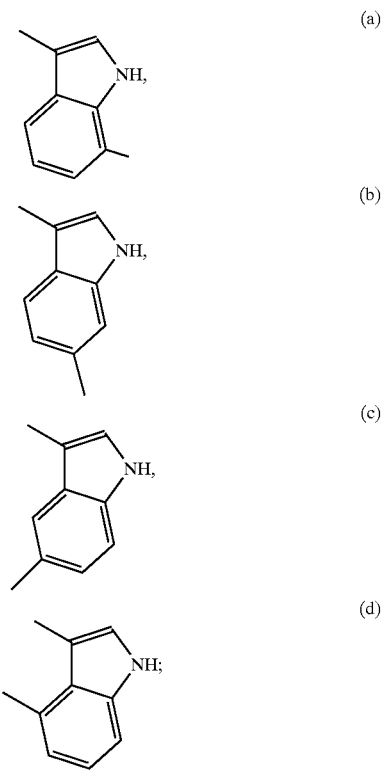

The present invention also includes compounds of formula (II), which are useful for preparing the compounds of formula (I):

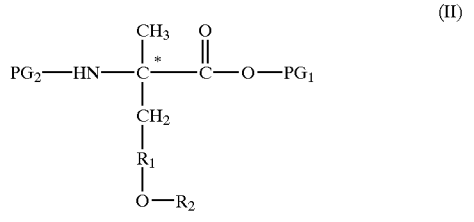

(II)

wherein $R_1$ is the same as indicated for the compounds of formula (I);

$R_2$ is H or a group —$R_3$—O—$R_4$, wherein $R_3$ is $C_1$–$C_7$ alkyl and $R_4$ is H or a leaving group, preferably a sulfonyl group such as tosyl, trifyl, mesyl, trimsyl, tripsyl, brosyl or nosyl;

$PG_1$ is a carboxyl protecting group; and $PG_2$ is an amino protecting group.

The present invention also includes a method of synthesizing compounds of formula (I) by reacting a compound of formula (IIc):

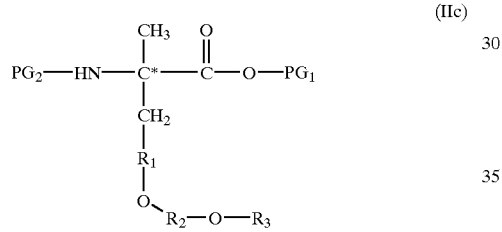

(IIc)

wherein $R_1$, $R_2$, $PG_1$ and $PG_2$ are the same as indicated for the compounds of formula (I), and $R_3$ is a leaving group, preferably a sulfonyl group such as tosyl, trifyl, mesyl, trimsyl, tripsyl, brosyl or nosyl, with a salt of RE, where RE is the same as indicated for the compounds of formula I, to produce a compound of formula (Ia):

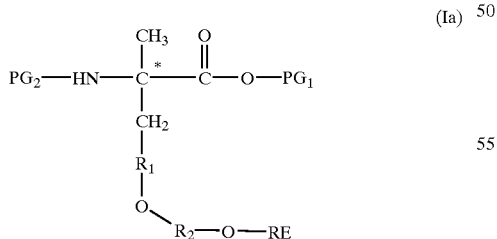

(Ia)

wherein $R_1$, $R_2$, RE, $PG_1$ and $PG_2$ are the same as above; and removing the protecting groups.

In this invention, compounds of formula I have been developed:

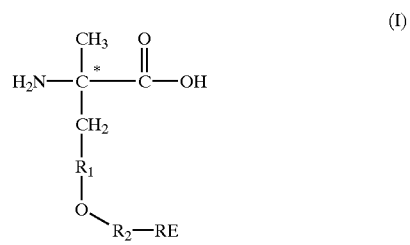

(I)

wherein the C marked with an asterisk represents a chiral center and the compound is present in the L-form, the D-form or as a racemic mixture; $R_1$ is selected from the group consisting of a single bond, phenyl, and a group of formula (a), (b), (c) or (d)

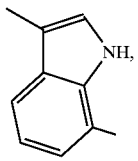

(a)

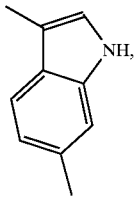

(b)

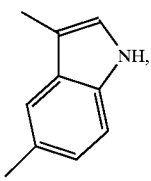

(c)

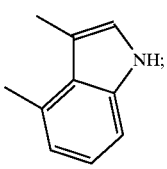

(d)

$R_2$ is $C_1$–$C_7$ alkyl; and

RE is selected from the group consisting of $^{11}C$, $^{13}N$, $^{15}O$, $^{18}F$, $^{67}Ga$, $^{75}Br$, $^{77}Br$, $^{123}I$, $^{124}I$, $^{125}I$, $^{126}I$, $^{131}I$, and $^{201}Tl$, preferably $^{123}I$, $^{125}I$, and $^{18}F$.

Preferably, $R_1$ is phenyl. When $R_1$ is phenyl, the —O—$R_2$—RE group can be para, meta or ortho the $CH_2$ group. It is preferred that the —O—$R_2$—RE group is para the $CH_2$ group.

$R_2$ is preferably $C_2$–$C_6$ alkyl, more preferably $C_2$–$C_5$ alkyl. It is most preferable that $R_2$ is propyl.

The compounds of formula (I) contain a chiral center at the α-C. The compounds of the invention can therefore be present in the L-form, the D-form, or as a racemic mixture. It is preferred that the compounds be present in the L-form.

The present invention also includes compounds of formula (II):

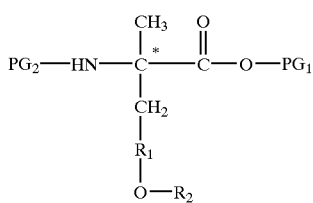

(II)

wherein
$R_1$ is the same as indicated for the compounds of formula (I);
$R_2$ is H or a group $—R_3—O—R_4$, wherein $R_3$ is $C_1-C_7$ alkyl and $R_4$ is H or a leaving group, preferably a sulfonyl group such as tosyl, trifyl, mesyl, trimsyl, tripsyl, brosyl or nosyl;
$PG_1$ is a carboxyl protecting group; and
$PG_2$ is an amino protecting group.

The compounds of formula (II) are useful as intermediates in the preparation of compounds of formula (I).

More specifically, the compounds of formula (II) may be divided into subgroups (IIa), (IIb) and (IIc):

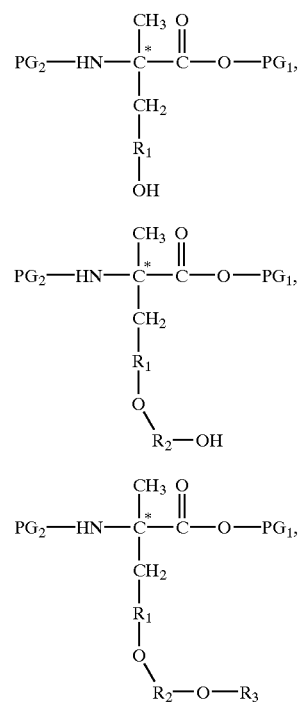

which are important intermediates in the preparation of compounds of formula (I),
wherein in each case
$R_1$ and $R_2$ are the same as indicated for the compounds of formula (I);
$R_3$ is a leaving group, preferably a sulfonyl group such as tosyl, trifyl, mesyl, trimsyl, tripsyl, brosyl or nosyl;
$PG_1$ is a carboxyl protecting group; and
$PG_2$ is an amino protecting group.

As noted above, the leaving groups for compounds of formula (II) are preferably sulfonyl groups, however any suitable leaving group can be used, as known to those of ordinary skill in the art. Especially preferred are tosyl, trifyl, mesyl, trimsyl, tripsyl, brosyl or nosyl, with tosyl, trifyl and mesyl being more preferred and tosyl being most preferred.

The protecting groups ($PG_1$ and $PG_2$) can be any suitable carboxyl protecting group and amino protecting group, as known to those of ordinary skill in the art. Reference is made to "Protective Groups in Organic Chemistry," ed. J. F. W. McOmie, Plenum Press, 1973; and T. W. Greene & P. G. M. Wuts, "Protective Groups in Organic Synthesis," John Wiley & Sons, 1991, each incorporated by reference. $PG_1$ may be, for example, an alkyl group such as methyl, ethyl or propyl. $PG_2$ may be, for example, a Boc group.

Generally, the reaction scheme for preparing compounds of formula (I) is as follows. A starting compound of formula (III):

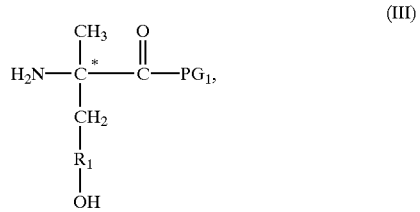

(III)

wherein $R_1$ and $PG_1$ are the same as indicated for the compounds if formula (I), such as α-methyl tyrosine $C_1-C_3$ alkyl ester, α-methyl serine $C_1-C_3$ alkyl ester or α-methyl hydroxy-tryptophan $C_1-C_3$ alkyl ester, is reacted in a suitable solvent with a compound providing a suitable protecting group $PG_2$, such as di-t-butyl dicarbonate (which provides a Boc group), to protect the amine, giving the compound of formula (IIa).

The compound of formula (IIa) is thereafter reacted in a suitable solvent with a halogenated $C_1-C_7$ alkanol, to give the compound of formula (IIb).

The compound of formula (IIb) is thereafter reacted in a suitable solvent with a halogenated leaving group, such as halogen-tosyl, to give the compound of formula (IIc).

The compound of formula (IIc) is reacted in a suitable solvent with a salt of RE, as defined above, such as K-$^{18}$F, to give the compound of formula (Ia). The compound of formula (Ia) is converted into the compound of formula (I) by removing the protecting groups ($PG_1$ and $PG_2$), for example by using TFA.

In the exemplified embodiment, 3-[$^{18}$F]fluoropropyl-α-methyl tyrosine, the radiochemical yield for the compound of the invention was much higher than $^{11}$C- and $^{18}$F-labeled amino acids synthesized using an electrophilic process. In addition, the compounds of the invention are stable and show high uptake in tumors. The compounds of the invention are useful to differentiate the degree of malignancy of tumors (e.g., brain, breast, prostate, colon, lung, liver, pancreas, gastric, lymphoma, uterine, cervical, extremitis, sarcoma and melanoma). The compounds of the invention are also useful to image neurological disorders (e.g. Alzheimer's, Huntington's), abscess, inflammation and infectious diseases. Suitable dosages are known or could be easily determined by those of ordinary skill in the art.

EXAMPLES

Experiment 1

Synthesis of N-t-Butyloxycarbonyl-α-methyltyrosine methylester

| α-Methyltyrosine HCl methylester | MW 245.7 |
| --- | --- |
| | Wt 2.54 g |
| | mmol 10.33 |
| Di-t-butyl dicarbonate | MW 218.25 |
| | Wt 2.20 g |
| | mmol 10.08 |
| Triethylamine | MW 101 |
| | Wt 2.50 g or 3.6 ml |
| | mmol 24.8 |

The α-methyltyrosine methylester (2.54 g) was dissolved in 16 ml of dimethylformamide (DMF) which became cloudy with the addition of triethylamine (3.6 ml). Di-t-butyl dicarbonate (2.20 g) was added and the mixture stirred overnight. After evaporation of DMF under high vacuum the material was treated with ether (30 ml) which produced a precipitate. This precipitate was filtered and discarded. Evaporation of the filtrate yielded 3.38 g (dried under vacuum) of a colorless liquid. TLC analysis using Hexane. Ethyl Acetate (1:1) showed the product at Rf 0.7 and the starting material at 0.1.

Experiment 2

Synthesis of N-t-Butyloxycarbonyl-O-[3-hydroxypropyl]-αmethyltyrosine methylester

| N-t-Butyloxycarbonyl-α-methyltyrosine methyl ester | MW 309.2 |
| --- | --- |
| | Wt 1.7 g |
| | mmol 5.50 |
| 3-Bromopropanol | MW 138.9 |
| | Wt 924 mg or 0.6 ml |
| | mmol 6.65 |
| Sodium ethoxide (NaOEt) | MW 68.05 |
| | Wt 742 mg |
| | mmol 10.90 |

The N-t-butyloxycarbonyl-α-methyltyrosine methylester (1.70 g) from the previous synthesis was dissolved in 25 ml of absolute ethanol and treated with dry sodiun ethoxide (742 mg). 3-Bromopropanol (924 mg, 0.6 ml) was added and the solution was refluxed for 5 hours. The ethanol was then evaporated, 100 ml of dichloromethane added and the solution washed with 100 ml of water. After drying over $MgSO_4$ the solvent was evaporated to yield two spots on a TLC plate developed in EtOAc:Hexane 1:1. The first spot was product and the second was starting material. The product was purified on a silica gel column using EtOAc:Hexane (1:1) A yield of 620 mg (MW 367.2, 31%) was obtained.

Experiment 3

Synthesis of N-t-Butyloxycarbonyl-O-[3-tosylpropyl]-α-methyltyrosine methylester

| N-t-Butyloxycarbonyl-O-[3-hydroxypropyl]-α-methyltyrosine Methylester | MW 367.2 |
| --- | --- |
| | Wt 620 mg |
| | mmol 1.69 |
| p-Toluenesulfonyl chloride (tosyl chloride) | MW 190.5 |
| | Wt 400 mg |
| | mmol 2.10 mg |
| Pyridine | MW 79 |
| d = 0.98 g/ml | Wt 500 mg |
| | mmol 6.33 |

The N-t-butyloxycarbonyl-O-[3-hydroxypropyl]-α-methyltyrosine methylester (620 mg) from the previous synthesis was dissolved in 10 ml of chloroform and carefully treated with p-toluenesulfonyl chloride (400 mg, which is tosyl chloride) and 0.5 ml of pyridine (500 mg). After allowing to react overnight the volume of solvent was reduced to 2 ml and added to a silica column for purification. The column was washed with EtOAc:Hexane 2:1 and the fractions #4–6 were combine to yield 400 mg, 45.4% of product. Analysis by TLC developed in EtOAc:hexane showed the product between the starting material and tosyl chloride.

Experiment 4

Synthesis of 3-$^{18}$F-fluoropropyl-α-methyltyrosine ([$^{18}$F]FPAMT)

Fluorine-18 in 1.0 milliliter of 95% oxygen-18 enriched water was transferred from the cyclotron target to an anion exchange column (in the OH form) where the $^{18}$F was trapped, and the $^{18}$O-water passed through and was collected in a bottle. The $^{18}$F was washed from the column with 1.5 milliliters of 0.01 molar potassium carbonate into a reaction vessel containing 26 mg of 2,2,2-Kryptofix. The resulting potassium fluoride/Kryptofix complex was subsequently dried, first by distillation under vacuum and then by azeotropic distillation of the remaining water with the addition of three 1.5 milliliter portions of acetonitrile.

The $^{18}$F complex was allowed to exchange with the tosyl group on 4 milligrams of N-t-butyloxycarbonyl-O-[3-tosylpropyl]-α-methyltyrosine methylester (tosyl precursor; PAMT-OTs) which was dissolved in 0.5 milliliters of acetonitrile (tube #1). This exchange took 15 minutes at 95° C.

The cooled acetonitrile solution was passed onto a dry normal 500 milligram silica column (Sep-Pak column (Not C-18)). This material was eluted (washed from the column) with 3 milliliters of diethyl ether into tube #2 where the solvents (ether/acetonitrile) were evaporated to about 1 milliliter.

Addition of 0.1 milliliter of trifluoroacetic acid for 20 minutes at room temperature was used to remove the protecting group. The solution was evaporated to dryness and 2 milliliters of water were added to this tube (#2). After warming (40° C.), the water solution was passed through a 0.22 micron filter for sterilization.

The final product was analyzed for sterility and by High Performance Liquid Chromatography and TLC for radiochemical purity.

Experiment 5

In Vitro Cellular Uptake Assay

Each well containing 50,000 breast cancer cells, cell line 13762 (0.5 ml/well) was added with 2 $\mu$Ci of $^{18}$F-FDG and $^{18}$F-FPAMT. After 0.5–4 hours incubation, the cells were washed with phosphate buffered saline 3 times and followed by trypsin to loosen the cells. The cells were counted by a gamma counter.

An increased uptake of $^{18}$F-FDG and $^{18}$F-FPAMT as a function of time was observed in the breast cancer cell line. $^{18}$F-FPAMT showed slightly higher uptake than $^{18}$F-FDG at 0.5 and 2 hours incubation.

Experiment 6

In Vivo Tissue Distribution

Fischer 344 tumor-bearing rats (weight 150–155 g) with tumor volume 1.2 cm were administered with $^{18}$F-FDG and $^{18}$F-FPAMT (10 µCi/rat, i.v.). Biodistribution studies were conducted at 30 min, 2 and 4 hours.

Tumor/blood and tumor/muscle ratios were increased as a function of time for both $^{18}$F-FDG and $^{18}$F-FPAMT. There was an increased bone uptake in $^{18}$F-FPAMT at 2 hours, suggesting in vivo defluorination might have occurred. Tables 1 and 2 show % of injected dose per gram of tissue weight (values shown represent the standard deviation from 3 animals).

TABLE 1

Biodistribution of $^{18}$F-FPAMT in Breast Tumor-Bearing Rats
% of injected $^{18}$F-FPAMT dose per organ or tissue

|  | 30 min | 2 h | 4 h |
| --- | --- | --- | --- |
| Blood | 0.638 ± 0.021 | 0.298 ± 0.032 | 0.081 ± 0.007 |
| Lung | 4.812 ± 0.457 | 0.541 ± 0.084 | 0.105 ± 0.008 |
| Liver | 6.542 ± 1.142 | 3.587 ± 0.500 | 0.930 ± 0.049 |
| Stomach | 0.440 ± 0.052 | 0.190 ± 0.024 | 0.070 ± 0.002 |
| Spleen | 0.404 ± 0.023 | 0.215 ± 0.029 | 0.067 ± 0.009 |
| Kidney | 8.060 ± 0.101 | 7.721 ± 1.027 | 1.467 ± 0.236 |
| Thyroid | 0.730 ± 0.126 | 0.860 ± 0.045 | 1.220 ± 0.260 |
| Muscle | 0.318 ± 0.043 | 0.154 ± 0.017 | 0.055 ± 0.012 |
| Intestine | 0.838 ± 0.058 | 0.627 ± 0.209 | 0.148 ± 0.015 |
| Tumor | 0.454 ± 0.016 | 0.312 ± 0.024 | 0.069 ± 0.003 |
| Bone | 0.447 ± 0.045 | 1.256 ± 0.117 | 1.502 ± 0.214 |
| Heart | 0.445 ± 0.019 | 0.219 ± 0.024 | 0.054 ± 0.007 |
| Tumor/Blood | 0.712 ± 0.013 | 1.079 ± 0.171 | 0.853 ± 0.036 |
| Tumor/Muscle | 1.464 ± 0.138 | 2.057 ± 0.176 | 1.322 ± 0.341 |
| Tumor/Lung | 0.095 ± 0.006 | 0.599 ± 0.079 | 0.658 ± 0.081 |

TABLE 2

Biodistribution of $^{18}$FDG in Breast Tumor-Bearing Rats
% of injected $^{18}$FDG dose per organ or tissue

|  | 30 min | 2 h | 4 h |
| --- | --- | --- | --- |
| Blood | 0.58 ± 0.044 | 0.47 ± 0.072 | 0.25 ± 0.017 |
| Lung | 0.62 ± 0.054 | 0.52 ± 0.137 | 0.23 ± 0.022 |
| Liver | 0.88 ± 0.144 | 0.85 ± 0.040 | 0.79 ± 0.039 |
| Spleen | 0.57 ± 0.068 | 0.45 ± 0.046 | 0.19 ± 0.012 |
| Kidney | 0.96 ± 0.123 | 0.85 ± 0.158 | 0.51 ± 0.037 |
| Muscle | 1.42 ± 0.087 | 0.69 ± 0.072 | 0.31 ± 0.048 |
| Bone | 0.30 ± 0.036 | 0.28 ± 0.013 | 0.22 ± 0.017 |
| Tumor | 0.90 ± 0.113 | 1.05 ± 0.111 | 0.69 ± 0.097 |
| Tumor/Blood | 1.57 ± 0.188 | 2.24 ± 0.204 | 2.41 ± 0.676 |
| Tumor/Muscle | 0.66 ± 0.066 | 1.52 ± 0.175 | 2.20 ± 0.158 |

The invention has been described herein with reference to certain preferred embodiments. However, as obvious variations thereon will become apparent to those skilled in the art, the invention is not to be considered as limited thereto.

We claim:

1. A compound of formula (I), or a pharmaceutically acceptable salt thereof:

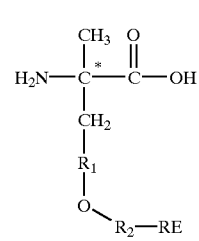

(I)

wherein the C marked with an asterisk represents a chiral center and the compound is present in the L-form, the D-form or as a racemic mixture;

$R_1$ is selected from the group consisting of a single bond, phenyl, and a group of formula (a), (b), (c) or (d)

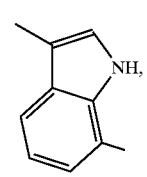

(a)

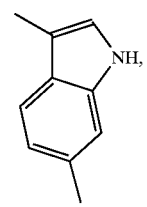

(b)

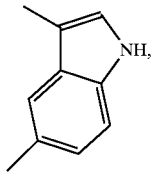

(c)

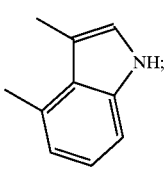

(d)

$R_2$ is $C_1$–C7 alkyl; and

RE is selected from the group consisting of $^{75}$Br, $^{124}$I and $^{18}$F.

2. The compound of claim 1, wherein $R_1$ is a single bond.
3. The compound of claim 1, wherein $R_1$ is phenyl.
4. The compound of claim 3, wherein the —O—$R_2$—RE group is para the $CH_2$ group on the phenyl.
5. The compound of claim 3, wherein the —O—$R_2$—RE group is meta the $CH_2$ group on the phenyl.
6. The compound of claim 3, wherein the —O—$R_2$—RE group is ortho the $CH_2$ group on the phenyl.
7. The compound of claim 1, wherein $R_1$ is a group of formula (a), (b), (C) or (d).
8. The compound of claim 1, wherein $R_2$ is $C_2$–$C_6$ alkyl.
9. The compound of claim 1, wherein $R_2$ is $C_2$–$C_5$ alkyl.
10. The compound of claim 1, wherein the compound is present in the L-form.
11. The compound of claim 1, wherein the compound is present in the D-form.

12. The compound of claim 1, wherein the compound is present as a racemic mixture.

13. The compound of claim 1, wherein the compound is 3-[$^{18}$F]fluoro($C_2$–$C_6$)-α-methyl tyrosine.

14. The compound of claim 13, wherein the compound is 3-[$^{18}$F]fluoropropyl-a-methyl tyrosine.

* * * * *